US006767532B2

(12) United States Patent
Dupuis et al.

(10) Patent No.: US 6,767,532 B2
(45) Date of Patent: Jul. 27, 2004

(54) COMPOSITION IN THE FORM OF AN AEROSOL MOUSSE BASED ON POLYURETHANE AND ANIONIC POLYMER

(75) Inventors: Christine Dupuis, Paris (FR); Claude Dubief, Le Chesnay (FR)

(73) Assignee: L'Oréal, Paris (FR)

( * ) Notice: Subject to any disclaimer, the term of this patent is extended or adjusted under 35 U.S.C. 154(b) by 292 days.

(21) Appl. No.: 10/120,453

(22) Filed: Apr. 12, 2002

(65) Prior Publication Data

US 2002/0197230 A1 Dec. 26, 2002

Related U.S. Application Data

(62) Division of application No. 09/265,850, filed on Mar. 11, 1999, now Pat. No. 6,383,472, which is a division of application No. 08/645,117, filed on May 13, 1996, now Pat. No. 6,080,392.

(30) Foreign Application Priority Data

May 12, 1995 (FR) ............................................. 95 05676

(51) Int. Cl.⁷ ................................................ A61K 7/11
(52) U.S. Cl. ............................. 424/47; 424/45; 424/59; 424/70.11; 424/70.13; 424/70.16; 424/DIG. 1; 424/DIG. 2
(58) Field of Search .......................... 424/45, 47, 70.11, 424/70.13, 70.16, 59, 78.03, DIG. 1, DIG. 2

(56) References Cited

U.S. PATENT DOCUMENTS

| | | | |
|---|---|---|---|
| 4,719,099 A | 1/1988 | Grollier et al. | 424/47 |
| 4,761,273 A | 8/1988 | Grollier et al. | 424/47 |
| 4,876,083 A | 10/1989 | Grollier et al. | 424/47 |
| 4,913,893 A | 4/1990 | Varco et al. | 424/47 |
| 4,983,377 A | 1/1991 | Murphy et al. | 424/47 |
| 5,002,985 A | 3/1991 | Anderson et al. | 524/45 |
| 5,039,519 A | 8/1991 | Inoue et al. | 424/70 |
| 5,053,218 A | 10/1991 | Shernov | 424/47 |
| 5,066,481 A | 11/1991 | Helioff et al. | 424/47 |
| 5,147,578 A | 9/1992 | Kirk | 252/358 |
| 5,297,566 A | 3/1994 | Firstenberg et al. | 132/203 |
| 5,362,486 A | 11/1994 | Nandagiri et al. | 424/71 |
| 5,385,729 A | 1/1995 | Prencipe et al. | 424/70.11 |
| 5,616,636 A | 4/1997 | Avar et al. | 524/102 |
| 5,620,684 A | 4/1997 | Dupuis | 424/70.12 |
| 5,626,840 A | 5/1997 | Thomaides et al. | 424/70.11 |
| 6,080,392 A * | 6/2000 | Dupuis et al. | 424/70.16 |
| 6,383,472 B1 * | 5/2002 | Dupuis et al. | 424/47 |

FOREIGN PATENT DOCUMENTS

| EP | 555155 | 8/1993 |
|---|---|---|
| EP | 636361 | 2/1995 |

* cited by examiner

Primary Examiner—Alton N. Pryor
(74) Attorney, Agent, or Firm—Finnegan, Henderson, Farabow, Garrett & Dunner, L.L.P.

(57) ABSTRACT

A cosmetic composition pressurized as an aerosol in the presence of a propellant and forming a mousse, comprising, in a cosmetically acceptable medium, at least one associative polyurethane and at least one anionic polymer, and to the use of an associative polyurethane in order to improve the properties of mousses based on anionic polymer and propellant.

1 Claim, No Drawings

COMPOSITION IN THE FORM OF AN AEROSOL MOUSSE BASED ON POLYURETHANE AND ANIONIC POLYMER

This is a division of application Ser. No. 09/265,850, filed on Mar. 11, 1999, now U.S. Pat. No. 6,383,472 which is a division of application Ser. No. 08/645,117, filed on May 13, 1996, now U.S. Pat. No. 6,080,392, the contents of which are incorporated herein by reference.

The present invention relates to a cosmetic composition pressurized as an aerosol in the presence of a propellant and capable of forming a mousse, comprising, in a cosmetically acceptable medium, at least one associative polyurethane and at least one anionic polymer. The invention also relates to the use of an associative polyurethane in order to improve the properties of mousses based on anionic polymer and propellant.

Cosmetic compositions pressurized in aerosol devices, under conditions such that they form a mousse on leaving the device, are well known and are used in particular in the treatment of the hair and/or the skin. Such compositions will be referred in the rest of the description as "aerosol mousses".

These mousses generally make it possible to obtain good distribution of the cosmetic compositions on the hair and they are, moreover, easy to use and more economical as regards the amount of product used when compared with lotions.

These mousses must be stable enough not to become liquified rapidly and must also disappear rapidly, either spontaneously or during massaging, which serves to redistribute the composition on and/or make it penetrate into keratin substances and more particularly the scalp and/or the hair.

Styling and/or holding mousses for the hair generally contain at least one polymer, preferably an anionic, nonionic or amphoteric one, which provides the hair with fixing properties.

These polymers are generally non-foaming or weakly-foaming ones and, in order to obtain an aerosol mousse, a foaming agent and/or an agent for improving the quality of the mousse must thus be added.

The foaming agents and/or the agents for improving the quality of the mousse usually used are, for example, anionic, nonionic or amphoteric surfactants; however, when used alone in combination with the polymer, these surfactants produce aerosol mousses of unsatisfactory quality. The reason for this is that they either become liquified at the time of application or they do not disappear after application even when massaged. Furthermore, a phenomenon of refoaming occurs on wet hair.

It has already been proposed, in French patent 2,505,348, to combine anionic polymers with cationic polymers, one of the two polymers having foaming properties.

It has also been proposed, in French patent 2,598,613, to use a polyvinyl alcohol as a foaming agent in cosmetic compositions.

The Inventors have now discovered that the properties of aerosol mousses based on anionic polymers can be improved by adding an associative polyurethane. In particular, the rigidity, the expansion and the stability of the mousse can be markedly improved.

The subject of the present invention is thus a cosmetic composition pressurized as an aerosol in the presence of a propellant and capable of forming a mousse, characterized in that it comprises, in a cosmetically acceptable aqueous medium, at least one associative polyurethane and at least one anionic polymer, at least one of the two polymers being a polymer with foaming power.

The subject of the invention is also a cosmetic composition in the form of a mousse, characterized in that it results from the expansion into the air of a composition as defined above.

The invention relates to the use of an associative polyurethane in order to improve the properties of mousses resulting from the expansion into the air of a composition pressurized as an aerosol based on anionic polymer and propellant, at least one of the two polymers being a polymer with foaming power.

Furthermore, the addition of the polyurethane can improve the cosmetic properties of the compositions pressurized as an aerosol containing an anionic polymer. Indeed, hair treated with the compositions according to the present invention can be softer and have a more natural and more pleasant feel. Moreover, the reinforcing effect of the compositions can be greater.

Furthermore, the mousses can be pleasant and easy to apply to keratin substances such as the hair or the skin.

The expression "polymer with foaming power" in accordance with the present invention refers to a polymer that, in solution in water at a concentration of 0.5% by weight, gives, according to the temperature-modified Ross Miles test (AFNOR standard T 73 404) carried out at 20° C., a mousse height of greater than 1 cm and, after pressurization of the solution, an amount of mousse such that the density is less than 0.4 and preferably less than 0.25 g/cm$^3$. These tests are described in French patent 2,505,348, the disclosure of which is incorporated herein by reference.

Preferably, the polymer with foaming power is the associative polyurethane and, even more particularly, the two polymers are polymers with foaming power.

Associative polyurethanes are preferably defined herein as polymers containing at least one hydrophilic sequence, at least one hydrophobic sequence and at least one urethane group.

The hydrophilic sequence is preferably a polyoxyalkylenated, and in particular polyoxyethylenated, sequence.

The hydrophobic sequence may be a fatty chain preferably comprising from 8 to 30 carbon atoms.

The associative polyurethane preferably contains at least two hydrophobic sequences.

As used herein, the term "hydrophobe" includes not only the hydrocarbon residues of hydroxyl, amino or isocyanage reactants but also the comination of such residues with next adjacent urethane and other groups remaining in the structure after reaction. The term "hydrophobe" or like term therefore is used herein to mean all of those portions or segments of the polymeric reaction products that contribute to water insolubility.

According to the invention, the associative polyurethanes generally have a molecular weight ranging from 500 to 5,000,000. As is clear to one skilled in the art, hen the Inventors refer to molecular weight, they intend to refer generically to both weight average molecular weight and number average molecular weight to the extent these terms differ. Unless expressly indicated to the contrary, references to molecular weight are to number average molecular weight.

Among the associative polyurethanes that may be used according to the invention, mention may be made of the polyurethanes belonging to one of the following three groups:

Group I

Polyurethanes corresponding to the following formula (I):

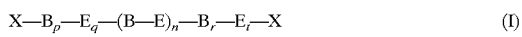

(I)

in which
n is a number ranging from 1 to 10, p, q, r and t, which may be identical or different, are equal to 0 or 1, with at least q or r equal to 1 and, t is equal to 0 when r is equal to 0,
with the proviso that:
when q is equal to 1, then:
a) p=r=t=0, or
b) p=0 and r=t=1, or
c) t=0 and r=p=1, and
when q is equal to 0, then:
r=1 and p=t=0;

Group II

Polyurethanes corresponding to the following formula (II):

(II)

in which
m is an integer ranging from 2 to 4 and s is an integer ranging from 0 to 2, the sum of m and s ranging from 2 to 4, w is an integer ranging from 1 to 3 and each of u, v and z is, independently of each other, 0 or 1; L represents Y, Z or —O—, Y being a hydrophobic hydrocarbon radical containing at least one carbon atom and preferably from 1 to 4 carbon atoms, and Z is a trivalent hydrophobic radical chosen from the following groups:
—OCONH(CH$_2$)$_6$N[CONH(CH$_2$)$_6$NHCOO—]$_2$,
CH$_3$C[CH$_2$O—OCNHC$_7$H$_6$NHCO—]$_3$, and
CH$_3$CH$_2$C[CH$_2$O—OCNHC$_7$H$_6$NHCO—]$_3$
Q represents the trivalent —CH$_2$C≡ group and D the —CH$_2$O— group, with the proviso that
a) when L represents Y, then u and w are each equal to 1, v and z are equal to 0, m is equal to at least 2 and the sum of m and s is 4;
b) when L is equal to Z, then u, v and s are each equal to 0, m is equal to 3, w is equal to 2 or 3 and z is 0 or 1; and
c) when L represents —O—, then v and u are each equal to 1, w ranges from 1 to 3, m is equal to 2 and s and z are each equal to 0;
in each of the formulae of these two groups X and R represent a hydrophobic radical;
B represents a hydrophobic divalent group of formula —CONH—G—NHCO—O—, in which G is a divalent radical derived from an organic di- or triisocyanate in which all the isocyanate groups have reacted; and E represents a nonionic divalent polyether group;

Group III

The polyurethanes of this group are obtained by reaction of (a) a polyfunctional reactant chosen from organic polyols possessing at least three hydroxyl groups, organic polyisocyanates possessing at least three isocyanate groups, and a mixture thereof; (b) a difunctional reactant chosen from organic diols, organic diisocyanates and a mixture thereof, the diol being present in the reaction mixture when the polyisocyanate is present and the diisocyanate being present when the polyol is present; (c) a hydroxyl or amino monofunctional compound in a sufficient amount to trap any isocyanate group which has not reacted during the reaction between (a) and (b), and in order to prevent coagulation of the reaction mixture; and, optionally, (d) an organic monoisocyanate in order to trap the hydroxyl groups remaining after the reaction between (a) and (b); in which reaction, at least either the polyol or the diol contains at least one water-soluble polyether segment with a molecular weight of at least 1500, the sum of the carbon atoms in the reactants containing isocyanate groups, hydroxyl groups and amino groups is at least 20, and the average molecular weight of these polyurethanes is approximately from 10,000 to 200,000.

Such associative polyurethanes are described, for example, in the following patents: U.S. Pat. Nos. 4,179,028, 4,155,892, 4,327,008, 4,337,184, 4,373,083, 4,499,233 and 4,426,485, the disclosures of which are incorporated herein by reference.

It is also possible to use the polyurethanes corresponding to the following formula (III):

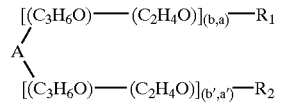

in which
[(C$_3$H$_6$O)—(C$_2$H$_4$O)]$_{(bi,ai)}$, with (bi,ai) denoting (b,a) or (b',a'), means that it is a statistical polymer of propylene oxide and ethylene oxide containing a moles of ethylene oxide and b moles of propylene oxide distributed randomly in the polymer chain, A denotes a divalent radical derived from an aliphatic, cycloaliphatic or aromatic diisocyanate, preferably a divalent radical derived from a polymethylene diisocyanate, toluene diisocyanate or methanediphenylene diisocyanate;
R$_1$ and R$_2$, which may be identical or different, denote a C$_8$–C$_{30}$, preferably C$_{10}$–C$_{20}$, and more particularly C$_{12}$–C$_{18}$ alkyl or alkenyl radical;
ai and bi, which may be identical or different, being such that the sum ai+bi ranges from 20 to 200 mol and preferably from 60 to 120 mol;
the ai/bi molar ratio ranges from 30/70 to 90/10, preferably from 50/50 to 90/10, and more preferably from 70/30 to 85/15.

The compounds of formula (III) that are particularly preferred are those in which A denotes a hexamethylene diisocyanate residue; R$_1$ and R$_2$ denote a lauryl radical or a mixture of radicals derived from tallow; the radicals Ri[(C$_3$H$_6$O)—(C$_2$H$_4$O)]$_{(bi,ai)}$ preferably have a molecular weight of about 4000 with Ri denoting R$_1$ or R$_2$ and ai and bi denoting a and b or a' and b' defined above.

Compounds of formula (III) that may be used according to the invention are described in European application EP 260,430 and marketed under the name Dapral T210 and Dapral T212 by the company AKZO.

Those particularly preferred are the polymers of Group I having the following formula (IV):

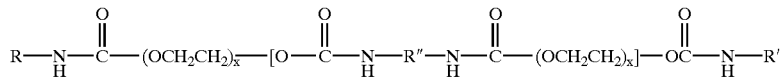

in which:

R and R', which may be identical or different, are $C_8$–$C_{18}$ hydrocarbon radicals R" is a $C_7$–$C_{36}$ hydrocarbon radical x ranges from 90 to 600, and n ranges from 1 to 4.

Examples of polymers of this type are the product pure Bermodol 2130 sold by the company Akzo Nobel, the products proposed under the names DW1206J, DW1206B and DW1206F by the company Seppic, and the products sold under the names Acrysol RM-2020, Acrysol RM-8, Acrysol RM-825 and Acrysol 44 by the company Seppic.

According to the invention, any foaming or non-foaming anionic polymer known per se may be used. Obviously, one or more anionic polymers may be used.

Thus, the anionic polymers generally used are polymers containing groups derived from carboxylic, sulphonic or phosphoric acid and having a molecular weight of approximately from 500 to 5,000,000.

The carboxylic groups are provided by unsaturated monocarboxylic or dicarboxylic acids such as those corresponding to the formula (V):

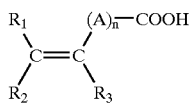

in which n is an integer from 0 to 10, A denotes a methylene group, optionally connected to the carbon atom of the unsaturated group or to the neighboring methylene group when n is greater than 1 via a hetero atom such as oxygen or sulphur, $R_1$ denotes a hydrogen atom or a phenyl or benzyl group, $R_2$ denotes a hydrogen atom or a lower alkyl or carboxyl group, $R_3$ denotes a hydrogen atom, a lower alkyl group or a —$CH_2$—COOH, phenyl or benzyl group. In the above-mentioned formula, a lower alkyl radical preferably denotes a group having 1 to 4 carbon atoms and, in particular, methyl and ethyl.

The preferred anionic polymers containing carboxylic groups according to the invention are:

A) the homo- or copolymers of acrylic or methacrylic acid or salts thereof and, in particular, the products sold under the names Versicol E or K by the company Allied Colloid and Ultrahold by the company BASF. Further, copolymers of acrylic acid and acrylamide are sold in the form of their sodium salt under the names Reten 421, 423 or 425 by the company Hercules, and the sodium salts of polyhydroxycarboxylic acids are also particularly useful.

B) the copolymers of acrylic or methacrylic acid with a monoethylenic monomer such as ethylene, styrene, vinyl esters or acrylic or methacrylic acid esters, optionally grafted onto a polyalkylene glycol such as polyethylene glycol and optionally crosslinked. Such polymers are described in particular in French patent 1,222,944 and German application 2,330,956, the disclosures of which are specifically incorporated by reference herein, copolymers of this type containing an optionally N-alkylated and/or hydroxyalkylated acrylamide unit in their chain, as described in particular in Luxembourg patent applications 75370 and 75371, the disclosures of which are specifically incorporated by reference herein, or as proposed under the name Quadramer by the company American Cyanamid. Mention may also be made of the copolymers of acrylic acid and $C_1$–$C_4$ alkyl methacrylate and the terpolymers of vinylpyrrolidone, acrylic acid and methacrylate of $C_1$–$C_{20}$ alkyl, for example of lauryl, such as that sold by the company ISP under the name Acrylidone LM. Mention may also be made of the copolymer of methacrylic acid and ethyl acrylate sold under the name Luvimer Maex by the company BASF.

C) copolymers derived from crotonic acid, such as those containing in their chain vinyl acetate or propionate units and optionally other monomers such as allylic or methallylic esters, vinyl ether or vinyl ester of a linear or branched saturated carboxylic acid containing a long hydrocarbon chain, such as those containing at least 5 carbon atoms, it being possible for these polymers to be optionally grafted and crosslinked, or alternatively a vinyl, allylic or methallylic ester of an α- or β-cyclic carboxylic acid. Such polymers are described in, inter alia, French patents 1,222,944, 1,580,545, 2,265,782, 2,265,781, 1,564,110 and 2,439,798, the disclosures of which are incorporated by reference herein. Commercial products entering into this class are the resins 28-29-30, 26-13-14 and 28-13-10 sold by the company National Starch.

D) polymers derived from maleic, fumaric or itaconic acid or anhydride with vinyl esters, vinyl ethers, vinyl halides, phenylvinyl derivatives, acrylic acid and its esters; these polymers may be esterified. Such polymers are described in particular in U.S. Pat. Nos. 2,047,398, 2,723,248 and 2,102,113 and GB patent 839,805, the disclosures of which are incorporated by reference herein, and in particular those sold under the names Gantrez AN or ES by the company ISP.

Polymers also entering into this class are the copolymers of maleic, citraconic or itaconic anhydride and of an allylic or methallylic ester optionally containing an acrylamide or methacrylamide group, an α-olefin, acrylic or methacrylic esters, acrylic or methacrylic acid or vinylpyrrolidone in their chain; the anhydride functions are monoesterified or monoamidated. These polymers are described, for example, in French patents 2,350,384 and 2,357,241, the disclosures of which are incorporated by reference herein, and E) polyacrylamides containing carboxylate groups.

The polymers comprising sulphonic groups are polymers containing vinylsulphonic, styrenesulphonic, naphthalenesulphonic or acrylamidoalkylsulphonic units.

These polymers may be chosen in particular from:

salts of polyvinylsulphonic acid having a molecular weight ranging from approximately 1000 to 100,000, as well as the copolymers with an unsaturated comonomer such as acrylic or methacrylic acid and the esters thereof, as well as acrylamide or derivatives thereof, vinyl ethers and vinylpyrrolidone.

The salts of polystyrenesulphonic acid, the sodium salts having a molecular weight ranging from approximately 500,000 to approximately 100,000, sold respectively under the names Flexan 500 and Flexan 130 by National Starch. These compounds are described in patent FR 2,198,719, the disclosure of which is incorporated by reference herein.

The salts of polyacrylamidesulphonic acids, those mentioned in U.S. Pat. No. 4,128,631, the disclosure of which is incorporated by reference herein, and more particularly the polyacrylamidoethylpropanesulphonic acid sold under the name Cosmedia Polymer HSP 1180 by Henkel.

According to the invention, the anionic polymers are preferably chosen from acrylic acid copolymers such as the acrylic acid/ethyl acrylate/N-tert-butylacrylamide terpolymer sold under the name Ultrahold Strong by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acid or anhydride with vinyl esters, vinyl ethers, vinyl halides, phenylvinyl derivatives, acrylic acid and its esters, such as the methyl vinyl ether/monoesterified maleic anhydride copolymer sold under the name Gantrez ES 425 by the company ISP, the copolymers of methacrylic acid and methyl methacrylate sold under the name Eudragit L by the company Rohm Pharma, the copolymer of methacrylic acid and ethyl acrylate sold under the name Luvimer Maex by the company BASF, the terpolymer of vinylpyrrolidone/acrylic acid/lauryl methacrylate sold under the name Acrylidone LM by the company ISP and the vinyl acetate/crotonic acid copolymer sold under the name Luviset CA 66 by the company BASF and the vinyl acetate/crotonic acid/polyethylene glycol terpolymer sold under the name Aristoflex A by the company BASF.

The anionic polymers most particularly preferred are chosen from the methyl vinyl ether/monoesteritied maleic anhydride copolymer sold under the name Gantrez ES 425 by the company ISP, the copolymers of methacrylic acid and methyl methacrylate sold under the name Eudragit L by the company Rohm Pharma, the copolymer of methacrylic acid and ethyl acrylate sold under the name Luvimer Maex by the company BASF and the terpolymer of vinylpyrrolidone/acrylic acid/lauryl methacrylate sold under the name Acrylidone LM by the company ISP.

According to the invention, it is also possible to use anionic polymers in the form of a latex or pseudolatex, that is to say in the form of a dispersion of insoluble polymer particles.

According to the invention, the associative polyurethane is generally present in proportions ranging from 0.01% to 5% by weight approximately relative to the total weight of the composition, and preferably from 0.05 to 3% by weight.

The anionic polymers are generally present in proportions ranging from 0.1% to 20% by weight approximately relative to the total weight of the composition and preferably from 0.5% to 8% by weight approximately relative to the total weight of the composition.

The cosmetically zacceptable medium preferably comprises water or a mixture of water and cosmetically acceptable solvents such as monoalcohols, polyalcohols, glycol ethers or fatty acid esters, which may be used alone or as a mixture.

Mention may be made more particularly of lower alcohols such as ethanol and isopropanol, polyalcohols such as diethylene glycol, glycol ethers and alkyl ethers of glycol or of diethylene glycol.

The pH of the compositions according to the invention is preferably from 2 to 9, and more preferably from 3 to 8. The pH may be adjusted to the chosen value by means of basifying or acidifying agents commonly used in cosmetics for this type of application.

The compositions according to the invention may also contain thickeners, surfactants, preserving agents, sequestering agents, softeners, fragrances, dyes, viscosity modifiers, pearlescent agents, moisturizing agents, antidandruff agents, anti-seborrhoeic agents, sunscreens, proteins, vitamins, plasticizers, hydroxy acids, electrolytes and fragrances.

The compositions according to the invention may also contain conditioners. These may then be chosen from natural or synthetic oils and waxes, fatty alcohols, esters of polyhydric alcohols, glycerides, silicone oils, gums and resins, polymers (cationic, nonionic or amphoteric) or mixtures of these various compounds.

A person skilled in the art will manifestly take care to choose the optional compound or compounds to be added to the composition according to the invention such that the advantageous properties intrinsically attached to the composition in accordance with the invention are not damaged, or are substantially not damaged, by the addition envisaged: in particular, optional ingredients should not prevent the production of the mousse nor diminish its properties.

The propellants are generally present in proportions of less than 25% by weight relative to the total weight of the composition and preferably in proportions from 1% to 10%.

The propellant may be chosen from volatile hydrocarbons, such as n-butane, propane, isobutane and pentane, chloro and/or fluoro hydrocarbons and mixtures thereof. Carbon dioxide, nitrous oxide, dimethyl ether, nitrogen or compressed air may also be used as propellant.

The compositions introduced into the aerosol device may be, for example, in the form of a lotion, dispersions or emulsions which, after distribution from the aerosol device, form mousses to be applied to the keratin substances such as the hair, the eyelashes or the skin.

The subject of the invention is also a process for the cosmetic treatment of keratin substances, such as the hair, characterized in that it comprises applying a cosmetic composition as defined above to the keratin substances and then in optionally rinsing with water, optionally after having left the cosmetic composition to stand on the keratin substances for a certain period.

Thus, this process according to the invention allows maintenance of the hairstyle or of the eyelashes and the treatment and care of the skin, the hair, the eyelashes or any other keratin substance.

The cosmetic compositions according to the invention may be used, for example, for the skin, the hair, the eyelashes or the eyebrows and preferably for the hair.

The compositions may more particularly be rinse-out or leave-in compositions, to be applied before or after shampooing, dyeing, bleaching, permanent-waving or straightening of the hair.

The compositions according to the invention are used even more particularly as fixing and/or styling compositions.

In the following text and in the preceding text, the percentages expressed are by weight.

The invention will now be illustrated more completely with the aid of the examples which follow, which should not be considered as limiting it to the embodiments described.

In the examples, AM means active material.

EXAMPLE 1

A styling mousse (A) according to the invention and two mousses B and C not in accordance with the invention, of the following compositions, were prepared:

| in g AM | A | B | C |
|---|---|---|---|
| Gantrez ES 425 | 1 | 1 | |
| Pure Bermodol 2130 | 0.2 | | 0.2 |
| AMP qs | pH 7.5 | pH 7.5 | pH 7.5 |
| Fragrance, dye | qs | qs | qs |
| Water qs | 100 | 100 | 100 |

The 3 compositions were packaged as follows:

Aerosol Packaging 90 g of the above compositions were packaged in an aerosol container in the presence of 10 g of a ternary mixture of n-butane, isobutane and propane (23/55/22), sold under the name "Aerogaz 3.2 N" by the company Elf Aquitaine. Gantrez ES 425 (ISP): methyl vinyl ether/monobutyl maleate copolymer Pure Bermodol 2130 from Akzo Nobel: associative polyurethane AMP: 2-amino-2-methyl-1-propanol The properties of these 3 mousses were evaluated by a panel of 5 experienced testers, and the results are collated in the table below.

| Properties | A (Invention) | B (Comparative) | C (Comparative) |
|---|---|---|---|
| Rigidity | 3.4 | 1.2 | 0.3 |
| Expansion | 5 | 3.2 | 1.8 |
| Stability | 5 | 1.2 | 1 |

Grading of the properties from 0 to 6:
0=none
6=excellent

The rigidity, stability and expansion properties of the mousse containing only the anionic polymer were markedly improved by the addition of an associative polyurethane.

The mousse (A) was also compared with four mousses (D, E, F and G) not in accordance with the invention, containing a non-associative polyurethane.

| in g AM | A | D | E | F | G |
|---|---|---|---|---|---|
| Gantrez ES 425 | 1 | 1 | 1 | | |
| Pure Bermodol 2130 | 0.2 | | | | |
| Uraflex XP 402 UZ | | 0.2 | | 0.2 | |
| Melio Promul 72 | | | 0.2 | | 0.2 |
| AMP qs | pH 7.5 | pH 7.5 | pH 7.5 | pH 7.5 | pH 7.5 |
| Fragrance, dye | qs | qs | qs | qs | qs |
| Water qs | 100 | 100 | 100 | 100 | 100 |

The aerosol packaging was identical for the 5 mousses and similar to that of Example 1.

Uraflex XP 402 UZ from DSM Resins: non-associative polyurethane Meilo Promul 72 from Quinn: non-associative polyurethane The properties of these 5 mousses were evaluated by a panel of 5 experienced testers, and the results are collated in the table below with the grading the same as in Example 1.

| Properties | A (Invention) | D (Comparative) | E (Comparative) | F (Comparative) | G (Comparative) |
|---|---|---|---|---|---|
| Rigidity | 3.4 | 1.2 | 0 | 0 | 0.2 |
| Expansion | 5 | 3.2 | 2.5 | 1.3 | 1.6 |
| Stability | 5 | 1.7 | 0.5 | 0 | 0.8 |

The rigidity, stability and expansion properties of the mousse containing only the anionic polymer were not improved by the addition of a non-associative polyurethane, even when the non-associative polyurethane has virtually identical properties to that of the associative polymer (mousses G and C).

EXAMPLE 4

A styling mousse having the following composition was prepared:

| | | |
|---|---|---|
| Methyl vinyl ether/monobutyl maleate copolymer Gantrez ES 425 (ISP) | | 4 g AM |
| Associative polyurethane (Acrysol 44 from Seppic) | | 0.5 g AM |
| Ethyl alcohol | | 17.3 g |
| 2-Amino-2-methyl-1-propanol | qs | pH 7.5 |
| Fragrance, dye | qs | |
| Demineralized water | qs | 100 g |

Aerosol Packaging 90 g of the above composition were packaged in an aerosol container in the presence of 10 g of a ternary mixture of n-butane, isobutane and propane (23/55/22), sold under the name "Aerogaz 3.2 N" by the company Elf Aquitaine.

The mousse exhibited good rigidity, stability and expansion properties. This mousse was applied to washed and drained hair. The hair was then dried by blow-drying. The hair treated with this composition according to the invention was soft and had a natural and pleasant feel.

EXAMPLE 5

A styling mousse of the following composition was prepared:

| | | |
|---|---|---|
| Methyl vinyl ether/monobutyl maleate copolymer Gantrez ES 425 (ISP) | | 2 g AM |
| Associative polyurethane (pure Bermodol 2130 from Akzo Nobel) | | 0.5 g AM |
| 2-Amino-2-methyl-1-propanol | qs | pH 7.5 |
| Fragrance, dye | qs | |
| Demineralized water | qs | 100 g |

Aerosol Packaging 90 g of the above composition were packaged in an aerosol container in the presence of 10 g of a ternary mixture of n-butane, isobutane and propane (23/55/22), sold under the name "Aerogaz 3.2 N" by the company Elf Aquitaine.

The composition had the same properties as that of Example 4.

EXAMPLE 6

A styling mousse of the following composition was prepared:

| | | |
|---|---|---|
| vinyl acetate/crotonic acid/vinyl neodecanoate terpolymer (Resin 28-29-30 from National Starch) | | 5 g AM |
| Associative polyurethane (Acrysol 44 from Seppic) | | 1 g AM |
| 2-Amino-2-methyl-1-propanol | qs | pH 7.5 |
| Fragrance, dye | qs | |
| Demineralized water | qs | 100 g |

Aerosol Packaging 90 g of the above composition were packaged in an aerosol container in the presence of 10 g of a ternary mixture of n-butane, isobutane and propane (23/55/22), sold under the name "Aerogaz 3.2 N" by the company Elf Aquitaine.

The composition had the same properties as that of Example 4.

EXAMPLE 7

A styling mousse of the following composition was prepared:

| | |
|---|---|
| Methyl vinyl ether/monobutyl maleate copolymer Gantrez ES 425 (ISP) | 0.5 g AM |
| Hydroxyethylcellulose/diallyldimethylammonium chloride copolymer sold under the name Celquat L 200 by the company National Starch | 0.5 g AM |
| Associative polyurethane (Acrysol 44 from Seppic) | 0.3 g AM |
| Ethyl alcohol | 10 g |
| 2-Amino-2-methyl-1-propanol | 0.15 g |
| Fragrance, dye | qs |
| Demineralized water | qs 100 g |

Aerosol Packaging 90 g of the above composition were packaged in an aerosol container in the presence of 10 g of HFC 134A (1,1,1,2-tetrafluoroethane).

The composition has the same properties as that of Example 4.

We claim:

1. A method of improving the properties of mousses resulting from the expansion into the air of a composition pressurized as an aerosol based on an anionic polymer and a propellant, comprising the step of including in said composition at least one associative polyurethane polymer comprising at least one hydrophilic sequence, at least one hydrophobic sequence and at least one urethane group, and wherein at least one of the two said polymers is a polymer with foaming power capable of forming the mousses.

* * * * *